United States Patent [19]

Gough

[11] 4,237,075

[45] Dec. 2, 1980

[54] FORMAMIDE CATALYSTS FOR REACTING PHOSPHORUS HALIDES WITH THIOLS

[75] Inventor: Stanley T. D. Gough, Whitehouse Station, N.J.

[73] Assignee: Mobil Oil Corporation, New York, N.Y.

[21] Appl. No.: 45,800

[22] Filed: Jun. 5, 1979

Related U.S. Application Data

[63] Continuation of Ser. No. 653,069, Jan. 28, 1976, abandoned, which is a continuation of Ser. No. 536,512, Dec. 26, 1974, abandoned.

[51] Int. Cl.$^3$ .......................... C07F 9/16; C07F 9/165; C07F 9/40; C07F 9/46
[52] U.S. Cl. ................................... 260/976; 260/972; 260/973

[58] Field of Search .................... 260/972, 973, 976

[56] References Cited

U.S. PATENT DOCUMENTS

| | | | |
|---|---|---|---|
| 3,607,991 | 9/1971 | Peterson et al. | 260/973 |
| 3,689,602 | 9/1972 | Ismail | 260/973 X |
| 3,803,272 | 4/1974 | Pivainer et al. | 260/973 |

*Primary Examiner*—Anton H. Sutto
*Attorney, Agent, or Firm*—Charles A. Huggett; Ronald J. Cier

[57] ABSTRACT

Formamides are catalysts for the reaction between phosphorus halides and alkanethiols, phenols, or thiophenols. As is described in U.S. Pat. No. 2,955,803, the phosphite and thiophosphite esters produced in the reaction are plant defoliants.

6 Claims, 2 Drawing Figures

FORMAMIDE CATALYSTS FOR REACTING PHOSPHORUS HALIDES WITH THIOLS

REFERENCE TO RELATED APPLICATIONS

This application is a continuation of copending application Ser. No. 653,069, filed Jan. 28, 1976, and now abandoned, which was a continuation of application Ser. No. 536,512 filed Dec. 26, 1974, now abandoned.

BACKGROUND OF THE INVENTION

1. Field of the Invention

This invention is concerned with a catalytic process for reaction of phosphorus halides with thiols.

2. Description of the Prior Art

It has been proposed in the art, such as in U.S. Pat. No. 2,955,803, to effect the reaction between a phosphorus halide (e.g., $PCl_3$) and a thiol (e.g., butanethiol) or phenol using a hydrogen halide acceptor, such as triethylamine or an alkali-metal hydroxide. This procedure is disadvantageous because it requires tedious product separation steps and, to be economically feasible, would require recovery and regeneration of the hydrogen halide acceptor.

Efforts have been made to remove hydrogen halide by applying a slight vacuum to the reaction system. This technique is commercially unattractive, because the reaction is sluggish and has a long induction period before hydrogen halide starts to evolve. This has been overcome to some extent by adding water to the reactants, but the reaction is still sluggish. Furthermore, water leads to turbidity and odor recurrence in the product and to the formation of pyrophoric sludges.

By the use of a formamide as a catalyst, the induction period is virtually eliminated. The formamide does not appear to be consumed in the reaction.

SUMMARY OF THE INVENTION

This invention provides a process for preparing esters of phosphorous acid phosphonous acid, or phosphinous acid, that comprises reacting (A) a compound having the formula: $R_nPCl_{3-n}$, wherein R is alkyl ($C_1$–$C_6$), phenyl with 0–2 methyl substituents, alkoxy ($C_1$–$C_6$), alkylthio ($C_1$–$C_6$), or phenoxy with 0–2 methyl substituents and n is 0–2, with (B) an alkanethiol ($C_1$–$C_6$), a benzenethiol with 0–2 methyl substituents, or a phenol with 0–2 methyl substituents, at a temperature between about 15° C. and about 100° C. and in the presence of between about 40 μl and about 2000 μl per mole of reactants of a formamide having the formula:

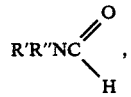

wherein R' and R" are the same or different and are H or alkyl ($C_1$–$C_3$).

This invention also provides, in said process for preparing esters of phosphorus, phosphonous or phosphinous acids, the improvement whereby the induction period of the reaction is virtually eliminated by carrying out the reaction in the presence of between about 40 μl and about 2000 μl per mole of reactants of a formamide catalyst having the formula:

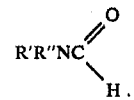

wherein R' and R" are the same or different and are H or alkyl ($C_1$–$C_3$).

DESCRIPTION OF SPECIFIC EMBODIMENTS

Figure 1:
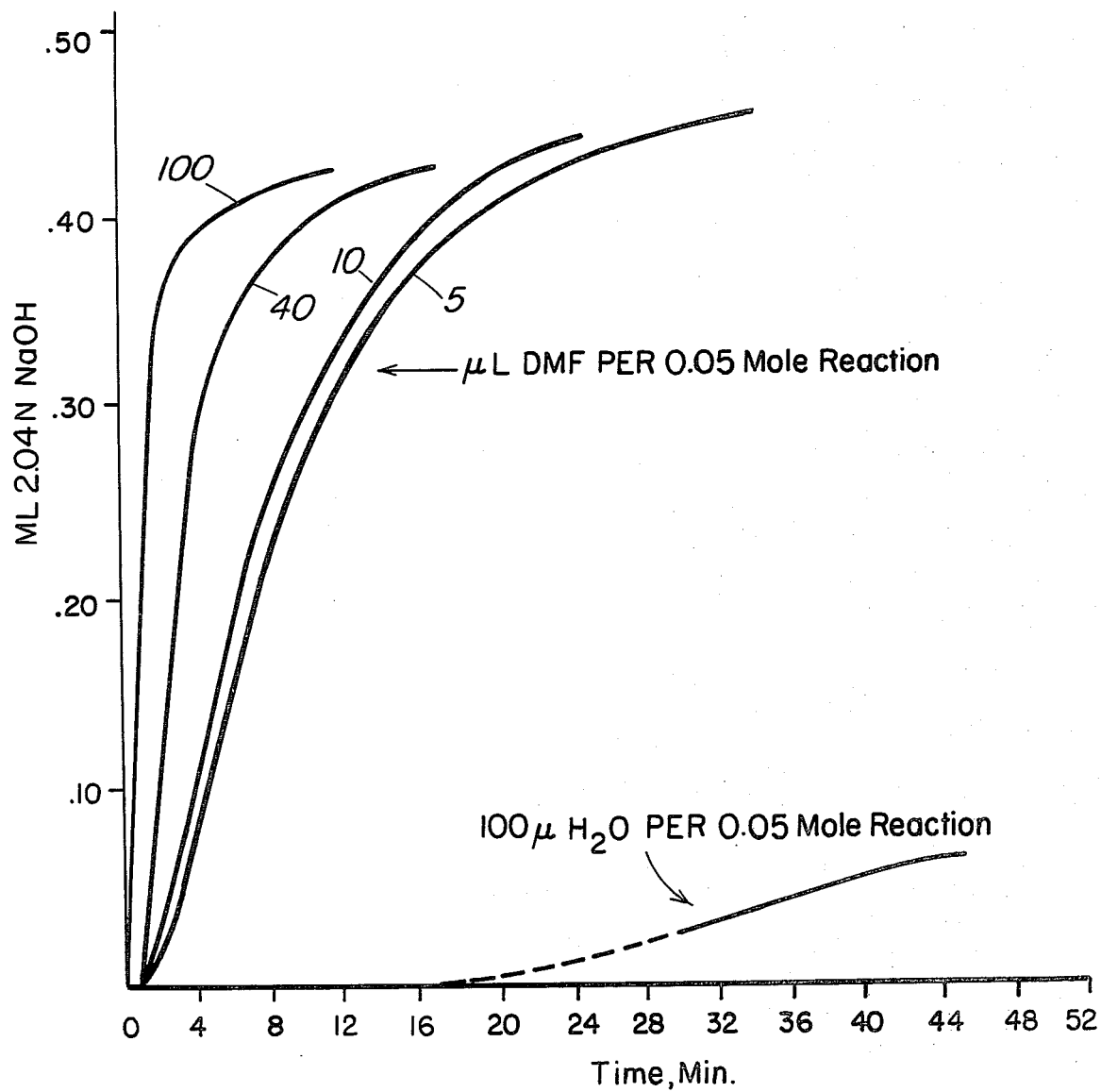
FIG. 1 presents a series of curves showing the relationship between the amount of reaction (as measured by HCl evolution) and time, at various dimethylformamide catalyst concentrations, in the reaction of $PCl_3$ with butanethiol and a similar, comparative curve for this relationship using water as an initiator.

The phosphorus chloride reactant has the general formula: $R_nPCl_{3-n}$, wherein R is alkyl ($C_1$–$C_6$), phenyl with 0–2 methyl substituents, alkoxy ($C_1$–$C_6$), alkylthio ($C_1$–$C_6$), or phenoxy with 0–2 methyl substituents and n is 0–2. When n is 0 the reactant will be $PCl_3$, which is preferred in making phosphite or trithiophosphite esters.

Other reactants within the scope of $R_nPCl_{3-n}$ are alkyl or phenyl phosphonous dichlorides ($RPCl_2$) such as methyl phosphonous dichloride, ethyl phosphonous dichloride, amyl phosphonous dichloride, phenyl phosphonous dichloride, and tolyl phosphonous dichloride; dialkyl or diphenyl phosphinous chlorides ($R_2PCl$) such as diisopropyl phosphinous chloride, dimethyl phosphinous chloride, dihexyl phosphinous chloride, and diphenyl phosphinous chloride; alkyl or phenyl phosphorodichloridites ($ROPCl_2$) such as methyl phosphorodichloride, butyl phosphorodichloridite, ethyl phosphorodichloridite, and phenyl phosphorochloridite; alkyl phosphorodichlorothioites ($RSPCl_2$), such as methyl phosphorodichlorothioite, propyl phosphorodichlorothioite, and amyl phosphorodichlorothioite; dialkyl or diphenyl phosphorochloridites [$(RO)_2PCl$] such as diethyl phosphorochloridite, dibutyl phosphorochloridite; and ditolyl phosphorochloridite; dialkyl phosphorochloridodithioites [$(RS)_2PCl$] such as dimethyl phosphorochloridodithioite, dipropyl phosphorochloridodithioite, and di-t-butyl phosphorochlorododithioite; alkyl alkylphosphonochloridites [$(RO)RPCl$] such as ethyl methylphosphonochlorodite and butyl methylphosphonochloridite; alkyl alkylphosphonochloridothioites [$(RS)RPCl$] such as amyl ethylphosphonochloridothioite, butyl butylphosphonochloridothioite, and methyl propylphosphonochloridothioite; and mixed S and O dialkyl phosphorochloroidothioites [$(RO)(RS)PCl$] such as O-methyl, S-butyl phosphorochloridothioite, O,S-dipropyl phosphorochloridothioite, and O,S-diamyl phosphorochloridothioite.

The phosphorus chloride reactant is reacted, according to the process of this invention, with an alkanethiol ($C_1$–$C_6$), a benzenethiol having 0–2 methyl substituents, or a phenol having 0–2 methyl substituents.

Non-limiting examples of these reactants are methanethiol, ethanethiol, propanethiol, isopropanethiol, butanethiol (butyl mercaptan), isobutanethiol, pentanethiol, 3-pentanethiol, hexanethiol, benzenethiol, o-toluenethiol, p-toluenethiol, 2,3-dimethylbenzenethiol, 2,5-dimethylbenzenethiol, phenol, o-cresol, p-cresol, 2,6-dimethylphenol, 2,5-dimethylphenol, and 3,5-dimethylphenol.

The reaction between the phosphorus chloride reactant and the thiol or phenol reactant, when reacted in full stoichiometric amounts, proceeds to the formation of esters of phosphorous acid, phosphonous acid, or phosphinous acid, e.g.:

$PCl_3 + 3RSH \rightarrow (RS)_3P + 3HCl$ $RPCl_2 + 2RSH \rightarrow RP(SR)_2 + 2HCl$ $R_2PCl + RSH \rightarrow R_2PSR + HCl$ The reaction can be carried out stepwise, however. This permits the preparation of a wide variety of mixed esters, e.g.:

$PCl_3 + RSH \rightarrow RSPCl_2 + HCl$ $RSPCl_2 + R'SH \rightarrow RS(R'S)PCl + HCl$ In each case the amount of reactants that is reacted is the stoichiometric amount for the desired reaction. In practice, however, between about 5 mole percent and about 25 mole percent excess thiol or phenol reactant is used.

The reaction is carried out at a temperature between about 15° C. and about 100° C. The reaction proceeds readily at room temperature (about 20° C.) but practically it is carried out at higher temperatures (about 75°-80° C.) by adding the phosphorus chloride reactant in increments over a period of time.

The catalyst used in the process of this invention is a formamide having the formula

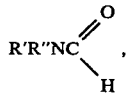

wherein R' and R" are the same or different and are H or alkyl ($C_1$-$C_3$). Non-limiting examples of utilizable formamides are formamide; N-methyl formamide; N,N-dimethyl formamide; N-ethylformamide; N-ethyl-N-methylformamide; N,N-diethylformamide; N-ethyl-N-isopropyl-formamide; and N,N-dipropyl-formamide.

These formamides are readily prepared by reacting formic acid with the appropriate monoalkylamine or dialkylamine (note, for example, U.S. Pat. No. 3,015,674).

N,N-dimethylformamide is preferred, primarily because it is readily available commercially. The amount of formamide used will be between about 40 μl and about 2000 μl per mole of reactants.

EXAMPLE 1

A series of runs were carried out to determine the effect of the amount of formamide on reaction rate, as measured by the evolution of HCl. In each run there was used 19 ml butanethiol and 4 ml phosphorus trichloride (a 0.05 mole reaction, using about 25% molar excess butanethiol). To each run was added a number of microliters (μl) of dimethyl formamide (DMF) and as HCl evolved the amount was measured by titration with 2.04 N NaOH at time intervals. The results are set forth in a series of curves showing ml NaOH vs minutes in FIG. 1. For comparison a run was made using 100 μl $H_2O$ and a curve plotted in FIG. 1.

From the curves in FIG. 1, it will be apparent that the use of DMF catalyst virtually eliminates the induction period and accelerates the reaction time. In comparison, the use of water initiator results in a long induction period and a slow reaction rate.

As indicated hereinbefore, it is preferred to operate by adding $PCl_3$ to butanethiol containing formamide catalyst at 75°-80° C. This is demonstrated in the following example.

EXAMPLE 2

In a reaction vessel were placed 101 ml butanethiol (0.75 mole plus 25 mole percent excess) and 50 μl (500 ppm) dimethylformamide. The reaction was carried out at about 78° C. by adding 22 ml $PCl_3$ (0.25 mole) in 1 ml increments over 2.5 hours. The evolution of HCl was followed by titration with 1.90 N NaOH. The results are plotted in the curve of FIG. 2 as ml NaOH vs time in minutes.

Figure 2:
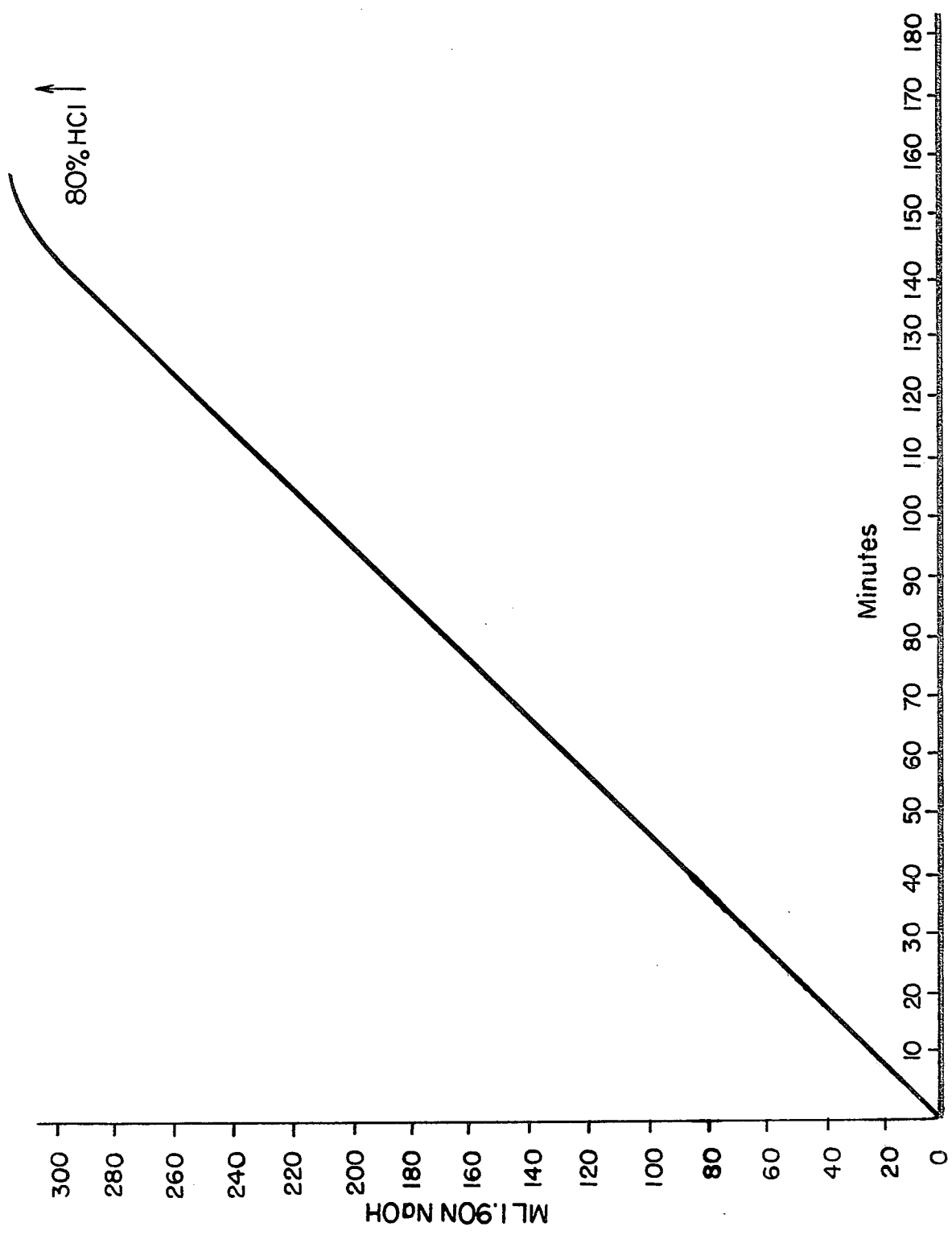
FIG. 2 presents a curve showing the relationship between the time and the amount of reaction obtained by the incremental addition of $PCl_3$ to butanethiol containing dimethylformamide catalyst.

From the curve in FIG. 2, it will be apparent that the reaction proceeds at a steady, good rate. After 150 minutes (2.5 hrs) the reaction has proceeded to 80 percent of theoretical.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. In the process for preparing esters of phosphorous acid, phosphonous acid, or phosphinous acid, which process comprises:
   (A) reacting a compound having the formula $R_nPCl_{3-n}$, wherein R is alkyl ($C_1$-$C_6$), alkoxy ($C_1$-$C_6$), or alkylthio ($C_1$-$C_6$) and n is 0-2; with
   (B) an alkanethiol ($C_1$-$C_6$);
   (C) at a temperature of between about 15° C. and about 100° C;
   (D) the improvement comprising virtually eliminating the induction period of the reaction by carrying out said process in the presence of a catalyst comprising a formamide having the formula:

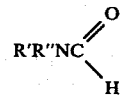

wherein R' and R" are the same or different and are H or alkyl ($C_1$-$C_3$).

2. The improved process of claim 1 wherein said compound having the formula $R_nPCl_{3-n}$ is phosphorus trichloride.

3. The improved process of claim 2 wherein said alkanethiol is butanethiol.

4. The improved process of claim 3 wherein said formamide having the formula:

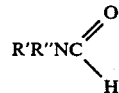

is dimethylformamide.

5. The improved process of claim 1 wherein, at higher temperatures, said reactant having the formula $R_nPCl_{3-n}$ is added to said alkanethiol reactant in increments over a period of time.

6. The improved process of claim 1 wherein said formamide catalyst is present in an amount of between about 40 μl and about 2000 μl per mole of reactants.

UNITED STATES PATENT AND TRADEMARK OFFICE
CERTIFICATE OF CORRECTION

PATENT NO. : 4,237,075
DATED : December 2, 1980
INVENTOR(S) : Stanley T.D. Gough It is certified that error appears in the above-identified patent and that said Letters Patent are hereby corrected as shown below:

Col. 2, line 51   "di-t'butyl" should read --di-$\underline{t}$-butyl--

Col. 3, line 2    "o-toluenethiol" should read --$\underline{o}$-toluenethiol--

Col. 3, line 3    "p-toluenethiol" should read --$\underline{p}$-toluenethiol--

Col. 3, line 4    "o-cresol" should read --$\underline{o}$-cresol--

Col. 3, line 4    "p-cresol" should read --$\underline{p}$-cresol--

Col. 3, line 68   "time" should be --rate--

Col. 4, line 32   "$R_nPCl_{3n}$" should be --$R_nPCl_{3-n}$--

Signed and Sealed this

Seventeenth Day of March 1981

[SEAL]

Attest:

RENE D. TEGTMEYER

Attesting Officer     Acting Commissioner of Patents and Trademarks